(12) United States Patent
Quincy, III

(10) Patent No.: US 7,794,486 B2
(45) Date of Patent: *Sep. 14, 2010

(54) THERAPEUTIC KIT EMPLOYING A THERMAL INSERT

(75) Inventor: Roger Bradshaw Quincy, III, Cumming, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1184 days.

This patent is subject to a terminal disclaimer.

(21) Appl. No.: 11/303,089

(22) Filed: Dec. 15, 2005

(65) Prior Publication Data

US 2007/0142883 A1  Jun. 21, 2007

(51) Int. Cl.
A61F 7/00 (2006.01)
A61F 7/02 (2006.01)

(52) U.S. Cl. .................... 607/114; 607/96; 607/108; 607/112

(58) Field of Classification Search ............... 607/96, 607/108, 114, 104
See application file for complete search history.

(56) References Cited

U.S. PATENT DOCUMENTS

| | | | |
|---|---|---|---|
| 2,573,791 | A | 11/1951 | Howells |
| 3,338,992 | A | 8/1967 | Kinney |
| 3,341,394 | A | 9/1967 | Kinney |
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,849,241 | A | 11/1974 | Butin et al. |
| 3,901,236 | A | 8/1975 | Assarsson et al. |
| 3,939,838 | A | 2/1976 | Fujinami et al. |

(Continued)

FOREIGN PATENT DOCUMENTS

DE  19545792 A1  6/1997

(Continued)

OTHER PUBLICATIONS

Article—*Adsorption of Gases in Multimolecular Layers*, Brunauer et al., The Journal of the American Chemical Society, vol. 60, Jan.-Jun. 1938, pp. 309-319.

(Continued)

Primary Examiner—Roy D Gibson
Assistant Examiner—Kaitlyn E Helling
(74) Attorney, Agent, or Firm—Dority & Manning, P.A.

(57) ABSTRACT

A therapeutic kit for providing heat to an area of the body is provided. The therapeutic kit may be used to treat a variety of injuries to muscles, ligaments, tendons, etc., including arm, leg, ankle, knee, shoulder, foot, neck, back, elbow, wrist, hand, chest, finger, toe injuries, and so forth. Regardless of its intended use, the therapeutic kit generally employs a pad that receives a thermal insert. The thermal insert includes a substrate containing an exothermic coating that is capable of generating heat in the presence of oxygen and moisture. One particular benefit of the thermal insert of the present invention is that it is disposable. Thus, when the thermal insert exhausts its heat-producing capacity, a new insert may simply be utilized. This allows for the continued use of the extensible material, resulting in substantial cost savings to the consumer.

33 Claims, 4 Drawing Sheets

U.S. PATENT DOCUMENTS

| | | |
|---|---|---|
| 3,955,565 A | 5/1976 | Johnson, Jr. |
| 4,041,203 A | 8/1977 | Brock et al. |
| 4,075,663 A | 2/1978 | Wellendorf |
| 4,100,324 A | 7/1978 | Anderson et al. |
| 4,286,082 A | 8/1981 | Tsubakimoto et al. |
| 4,323,534 A | 4/1982 | DesMarais |
| 4,340,563 A | 7/1982 | Appel et al. |
| 4,341,216 A | 7/1982 | Obenour |
| 4,374,888 A | 2/1983 | Bornslaeger |
| 4,423,118 A | 12/1983 | Corbett et al. |
| 4,628,918 A | 12/1986 | Johnson, Jr. |
| 4,655,760 A | 4/1987 | Morman et al. |
| 4,657,802 A | 4/1987 | Morman |
| 4,663,220 A | 5/1987 | Wisneski et al. |
| 4,720,415 A | 1/1988 | Vander Wielen et al. |
| 4,758,239 A | 7/1988 | Yeo et al. |
| 4,766,029 A | 8/1988 | Brock et al. |
| 4,781,966 A | 11/1988 | Taylor |
| 4,789,699 A | 12/1988 | Kieffer et al. |
| 4,834,738 A | 5/1989 | Kielpikowski et al. |
| 4,899,749 A * | 2/1990 | Laroco ............... 607/111 |
| 4,965,122 A | 10/1990 | Morman |
| 4,981,135 A * | 1/1991 | Hardy ............... 607/108 |
| 4,981,747 A | 1/1991 | Morman |
| 5,093,422 A | 3/1992 | Himes |
| 5,114,781 A | 5/1992 | Morman |
| 5,116,662 A | 5/1992 | Morman |
| 5,161,686 A | 11/1992 | Weber et al. |
| 5,165,402 A | 11/1992 | McCoy |
| 5,169,706 A | 12/1992 | Collier, IV et al. |
| 5,213,881 A | 5/1993 | Timmons et al. |
| 5,226,992 A | 7/1993 | Morman |
| 5,252,657 A * | 10/1993 | Frankel et al. ............ 524/460 |
| 5,272,236 A | 12/1993 | Lai et al. |
| 5,278,272 A | 1/1994 | Lai et al. |
| 5,284,703 A | 2/1994 | Everhart et al. |
| 5,304,599 A | 4/1994 | Himes |
| 5,306,487 A | 4/1994 | Karapasha et al. |
| 5,314,455 A | 5/1994 | Johnson, Jr. et al. |
| 5,316,837 A | 5/1994 | Cohen |
| 5,332,613 A | 7/1994 | Taylor et al. |
| 5,336,545 A | 8/1994 | Morman |
| 5,350,624 A | 9/1994 | Georger et al. |
| 5,366,491 A | 11/1994 | Ingram et al. |
| 5,382,400 A | 1/1995 | Pike et al. |
| 5,385,775 A | 1/1995 | Wright |
| 5,398,667 A | 3/1995 | Witt |
| 5,415,624 A | 5/1995 | Williams |
| 5,418,945 A | 5/1995 | Carter et al. |
| 5,464,688 A | 11/1995 | Timmons et al. |
| 5,539,056 A | 7/1996 | Yang et al. |
| 5,562,994 A | 10/1996 | Abba et al. |
| 5,596,052 A | 1/1997 | Resconi et al. |
| 5,599,585 A | 2/1997 | Cohen |
| 5,628,737 A | 5/1997 | Dobrin et al. |
| 5,656,355 A | 8/1997 | Cohen |
| 5,693,385 A | 12/1997 | Parks |
| 5,728,146 A | 3/1998 | Burkett et al. |
| 5,834,114 A | 11/1998 | Economy et al. |
| 5,836,932 A | 11/1998 | Buell et al. |
| 5,843,057 A | 12/1998 | McCormack |
| 5,855,999 A | 1/1999 | McCormack |
| 5,879,378 A * | 3/1999 | Usui ............... 607/96 |
| 5,890,486 A | 4/1999 | Mitra et al. |
| 5,906,879 A | 5/1999 | Huntoon et al. |
| 5,918,590 A | 7/1999 | Burkett et al. |
| 5,932,497 A | 8/1999 | Morman et al. |
| 5,984,995 A | 11/1999 | White |
| 5,997,981 A | 12/1999 | McCormack et al. |
| 6,002,064 A | 12/1999 | Kobylivker et al. |
| 6,015,764 A | 1/2000 | McCormack et al. |
| 6,019,782 A | 2/2000 | Davis et al. |
| 6,037,281 A | 3/2000 | Mathis et al. |
| 6,099,556 A * | 8/2000 | Usui ............... 607/114 |
| 6,111,163 A | 8/2000 | McCormack et al. |
| 6,114,024 A | 9/2000 | Forte |
| 6,149,934 A | 11/2000 | Krzysik et al. |
| 6,153,209 A | 11/2000 | Vega et al. |
| 6,197,045 B1 | 3/2001 | Carson |
| 6,198,018 B1 | 3/2001 | Curro |
| 6,203,810 B1 | 3/2001 | Alemany et al. |
| 6,245,401 B1 | 6/2001 | Ying et al. |
| 6,322,530 B1 | 11/2001 | Johnson, Jr. et al. |
| 6,420,625 B1 | 7/2002 | Jones et al. |
| 6,461,457 B1 | 10/2002 | Taylor et al. |
| 6,463,934 B1 | 10/2002 | Johnson, Jr. et al. |
| 6,517,906 B1 | 2/2003 | Economy et al. |
| 6,573,212 B2 | 6/2003 | McCrae et al. |
| 6,576,810 B1 | 6/2003 | Underhill et al. |
| 6,599,262 B1 * | 7/2003 | Masini ............... 602/2 |
| 6,639,004 B2 | 10/2003 | Falat et al. |
| 6,713,414 B1 | 3/2004 | Pomplum et al. |
| 6,770,064 B1 | 8/2004 | Ruscher |
| 6,863,682 B2 | 3/2005 | Usui |
| 6,915,798 B2 * | 7/2005 | Minami ............... 126/263.02 |
| 6,926,688 B2 | 8/2005 | Meyer |
| 6,938,793 B2 | 9/2005 | Lerner |
| 6,945,944 B2 | 9/2005 | Kuiper et al. |
| 2002/0141961 A1 | 10/2002 | Falat et al. |
| 2004/0138598 A1 | 7/2004 | Kortuem et al. |
| 2004/0153016 A1 | 8/2004 | Salmon et al. |
| 2004/0166248 A1 | 8/2004 | Hu et al. |
| 2004/0167447 A1 | 8/2004 | Johnson, III |
| 2004/0236261 A1 | 11/2004 | McCarthy et al. |
| 2005/0098466 A1 | 5/2005 | Thomas |
| 2005/0113771 A1 | 5/2005 | MacDonald et al. |
| 2005/0235653 A1 | 10/2005 | Valbh et al. |
| 2006/0141882 A1 | 6/2006 | Quincy et al. |
| 2006/0142712 A1 | 6/2006 | Quincy |
| 2006/0142828 A1 | 6/2006 | Schorr et al. |

FOREIGN PATENT DOCUMENTS

| | | |
|---|---|---|
| EP | 0348978 | 6/1989 |
| GB | 316878 A | 6/1930 |
| WO | WO 9827079 | 7/1998 |
| WO | PCT 9909918 A | 3/1999 |
| WO | WO 9912734 | 3/1999 |
| WO | WO 0040186 A1 | 7/2000 |
| WO | PCT 0103619 A | 1/2001 |

OTHER PUBLICATIONS

Article—*Heat-Generating Composite Material: Fe Oxidation in Fibers of a Polymer Matrix*, Babievskaya et al., Inorganic Materials, vol. 40, No. 1, 2004, pp. 35-43.

Article—*Phase Composition of the Products of Fe Oxidation in Fe + C +NaCl + $H_2O$ Exothermic Mixtures*, Babievskaya et al., Inorganic Materials, vol. 38, No. 6, 200, pp. 586-596.

Article—*Role of Activated Carbon in Chemical Interactions in the Fe-C-NaCl-$H_2O$-$O_2$ Heat-Generating System*, Drobot et al., Inorganic Materials, vol. 38, No. 5, 2002, pp. 501-506.

International Search Report dated Feb. 9, 2007 for International Application No. PCT/US2006/038814 filed Oct. 4, 2006.

Search Report and Written Opinion for PCT/US2006/046496, Apr. 19, 2007.

* cited by examiner

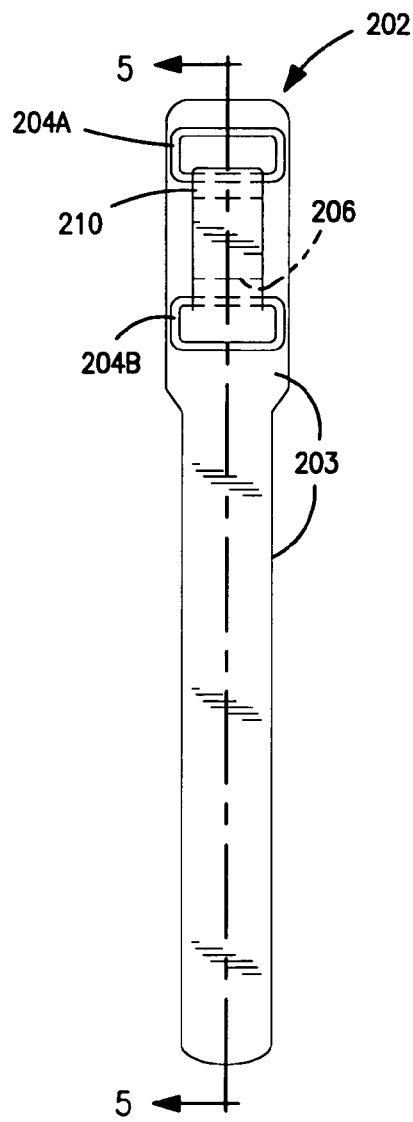
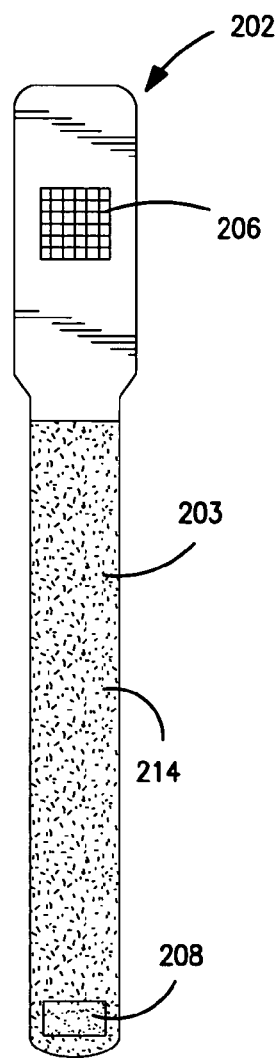
FIG. 3  FIG. 4
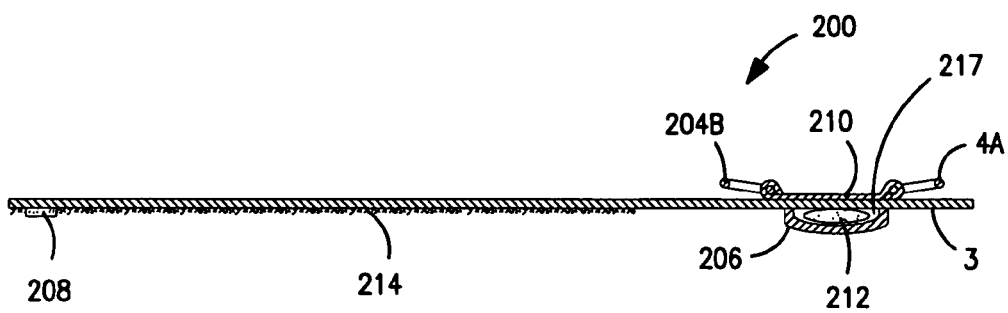
FIG. 5

THERAPEUTIC KIT EMPLOYING A THERMAL INSERT

BACKGROUND OF THE INVENTION

Therapeutic pads or packs are often used to warm muscles or reduce cramping. Most conventional pads require the use of external heating or reactants that undergo an exothermic reaction when mixed (i.e., chemical pads). "Bag-in-bag" chemical pads, for example, typically possess a smaller bag containing one reactant that is encompassed by a larger bag containing the other reactant. However, such chemical pads have a large surface area between the first reactant and the second reactant. Thus, the likelihood that the reactants will prematurely migrate through the smaller bag is increased. Although migration may be slowed with thicker materials, this sometimes results in an increased difficulty to rupture the material. Contrary to "bag-in-bag" chemical pads, "side-by-side" pads use a breakable seal that is positioned between two compartments, each of which contains one of the reactants. These pads attempt to use a strong exterior seal around the perimeter of the bag and a weak interior seal between the two compartments. However, this is difficult to achieve on a consistent basis and any rupturing of the exterior seal may cause a leak of the reactants onto the user.

As such, a need continues to exist for therapeutic pads that are easy to use and achieve consisting heating of a desired body part.

SUMMARY OF THE INVENTION

In accordance with one embodiment of the present invention, a therapeutic kit is disclosed that comprises a pad that defines a cavity and a thermal insert that is capable of being removably positioned within the cavity. The thermal insert comprises a substrate that contains an exothermic coating. The exothermic coating comprises an oxidizable metal. The exothermic coating is activatable upon exposure of the exothermic coating to oxygen and moisture to generate heat.

In accordance with another embodiment of the present invention, a method for providing heat to a body part is disclosed. The method comprises providing a thermal insert that contains an exothermic coating, wherein the thermal insert is sealed within an enclosure that inhibits the passage of oxygen to the exothermic coating. The enclosure is opened and positioned within a cavity defined by a pad. The pad is placed adjacent to or near a body part.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 3 is a top view of one embodiment of a therapeutic kit of the present invention;

FIG. 4 is a bottom view of the kit of FIG. 3;

FIG. 5 is a cross-sectional view of FIG. 3 taken along a line 5-5;

DETAILED DESCRIPTION OF REPRESENTATIVE EMBODIMENTS

Definitions

Figure 1:
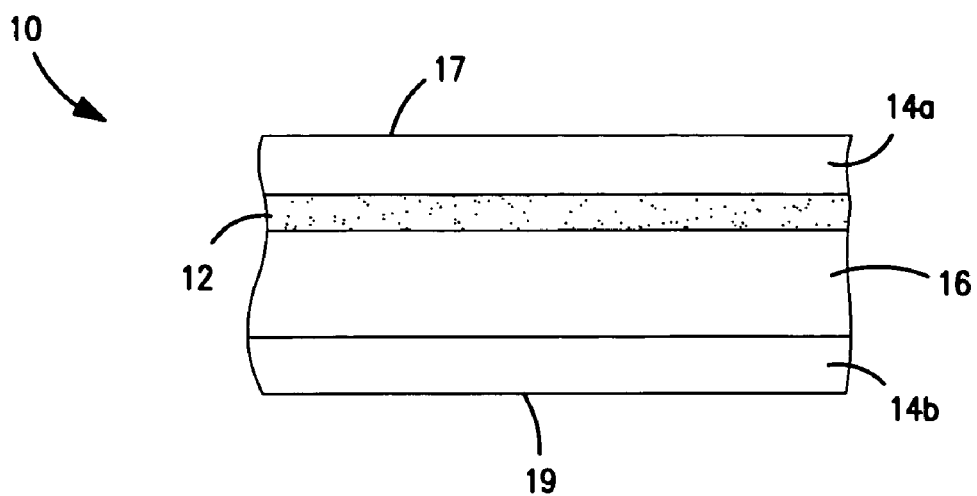
FIG. 1 illustrates a cross-sectional view of one embodiment of a thermal insert of the present invention.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbonded fibers are generally not tacky when they are deposited onto a collecting surface. Spunbonded fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "elastomeric" and "elastic" refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, such elastomeric sheet contracts or recovers at least 50%, and even more desirably, at least 80% of the stretch length in the cross machine direction.

As used herein, the "water vapor transmission rate" (WVTR) generally refers to the rate at which water vapor permeates through a material as measured in units of grams per meter squared per 24 hours ($g/m^2/24$ hrs). The test used to determine the WVTR of a material may vary based on the nature of the material. For instance, in some embodiments, WVTR may be determined in general accordance with ASTM Standard E-96E-80. This test may be particularly well suited for materials thought to have a WVTR of up to about 3,000 $g/m^2/24$ hrs.

Another technique for measuring WVTR involves the use of a PERMATRAN-W 100K water vapor permeation analysis system, which is commercially available from Modern Controls, Inc. of Minneapolis, Minn. Such a system may be particularly well suited for materials thought to have a WVTR of greater than about 3,000 $g/m^2/24$ hrs. However, as is well known in the art, other systems and techniques for measuring WVTR may also be utilized.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Breathable materials may, for example, have a water vapor transmission rate (WVTR) of at least about 100 grams per square meter per 24 hours ($g/m^2/24$ hours), in some embodiments from about 500 to about 20,000 $g/m^2/24$ hours, and in some embodiments, from about 1,000 to about 15,000 $g/m^2/24$ hours.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a therapeutic kit configured to provide heat to an area of the body. The therapeutic kit may be used to treat a variety of injuries to muscles, ligaments, tendons, etc., including arms, legs, ankles, knees, shoulders, feet, necks, backs, elbows, wrists, hands, chests, fingers, toes, and so forth. Regardless of its intended use, the therapeutic kit generally employs a pad that is capable of receiving a thermal insert. The thermal insert includes a substrate containing an exothermic coating that is capable of generating heat in the presence of oxygen and moisture. One particular benefit of the thermal insert of the present invention is that it is disposable. Thus, when the thermal insert exhausts its heat-producing capacity, a new insert may simply be utilized in the kit. This allows for the continued use of the pad, resulting in substantial cost savings to the consumer.

The pad used in the therapeutic kit of the present invention may be formed in a variety of ways as is known in the art. For example, the pad may contain an extensible material that is generally conformable to a body part of interest and capable of providing a user with a comfortable fit without restricting blood flow. Any type of extensible material may be used for this purpose. For instance, the extensible material may be a nonwoven web, woven fabric, knit fabric, paper, film, foam, etc. When utilized, the nonwoven web may be a spunbond web (apertured or non-apertured), meltblown web, bonded carded web, airlaid web, coform web, hydraulically entangled web, and so forth. Polymers suitable for making nonwoven webs include, for example, polyolefins, polyesters, polyamides, polycarbonates, copolymers and blends thereof, etc. Suitable polyolefins include polyethylene, such as high density polyethylene, medium density polyethylene, low density polyethylene, and linear low density polyethylene; polypropylene, such as isotactic polypropylene, atactic polypropylene, and syndiotactic polypropylene; polybutylene, such as poly(1-butene) and poly(2-butene); polypentene, such as poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, etc., as well as blends and copolymers thereof. Suitable polyesters include poly(lactide) and poly(lactic acid) polymers as well as polyethylene terephthalate, polybutylene terephthalate, polytetramethylene terephthalate, polycyclohexylene-1,4-dimethylene terephthalate, and isophthalate copolymers thereof, as well as blends thereof. It should be noted that the polymer(s) may also contain other additives, such as processing aids or treatment compositions to impart desired properties to the fibers, residual amounts of solvents, pigments or colorants, and so forth.

If desired, the extensible material may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety (e.g., poly(vinyl arene)) and wherein B is an elastomeric polymer midblock, such as a conjugated diene or a lower alkene polymer (e.g., polystyrene-poly(ethylene-butylene)-polystyrene block copolymers). Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer. Commercially available A-B-A' and A-B-A-B copolymers include several different formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S or styrene-poly(ethylene-propylene)-styrene elastomeric copolymer available from Kuraray Company, Ltd. of Okayama, Japan, under the trade name SEPTON®.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. Nos. 5,539,056 to Yang, et al. and 5,596,052 to Resconi, et al., which are incorporated herein in their entirety by reference thereto for all purposes.

The extensible material may also contain a film that is liquid- and vapor-impermeable, liquid- and vapor-permeable, or liquid-impermeable but vapor-permeable (i.e., "breathable"). The film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers. The film may also contain an elastomeric polymer, such as described above.

The extensible material may also have a multi-layered structure. Suitable multi-layered materials may include, for instance, spunbond/meltblown/spunbond (SMS) laminates and spunbond/meltblown (SM) laminates. Various examples of suitable SMS laminates are described in U.S. Pat. Nos. 4,041,203 to Brock et al.; 5,213,881 to Timmons, et al.; 5,464,688 to Timmons, et al.; 4,374,888 to Bornslaeger; 5,169,706 to Collier, et al.; and 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Multi-layered elastic laminates may also be employed in the extensible material. Elastic laminate may, for instance, include a film attached to a nonwoven web. One suitable elastic laminate is a neck-bonded laminate, which may contain a necked nonwoven web attached to an elastic film. Some examples of neck-bonded laminates are described in U.S. Pat. Nos. 5,226,992, 4,981,747, 4,965,122, and 5,336,545, all to Morman, which are incorporated herein in their entirety by reference thereto for all purposes. Another suitable elastic laminate is a stretch-bonded laminate, which may contain a nonwoven web that is attached to an elastic film in an extended condition. Suitable stretch-bonded laminate are described in U.S. Pat. Nos. 4,720,415 to Vander Wielen, et al.; 5,385,775 to Wright; 4,789,699 to Kieffer et al., 4,781,966 to Taylor, 4,657,802 to Morman, and 4,655,760 to Morman et al., which are incorporated herein in their entirety by reference thereto for all purposes. The elastic laminate may also be a necked stretch bonded laminate. Examples of necked stretch bonded laminates are disclosed in U.S. Pat. Nos. 5,114,781 and 5,116,662, which are both incorporated herein in their entirety by reference thereto for all purposes.

As stated above, the pad of the present invention is capable of receiving a thermal insert to provide heat to a desired body part. In some embodiments, for example, the pad defines a cavity into which the thermal insert may be removably positioned. The size and shape of the cavity is configured to accommodate the thermal insert. If desired, the cavity may be formed from a separate receptacle (e.g., pocket, pouch, etc.) that is attached to the extensible material with stitching, adhesive, thermal bonds, etc. Such a receptacle may be formed from an extensible material that will conform to the thermal insert and thereby help prevent its unintended removal. Once positioned within the cavity, the pad may then be placed adjacent to or near a body part to impart the desired level of heating. In some cases, the pad may be wrapped around the body part and fastened so that heating may be imparted without requiring that the user hold the pad.

Referring to FIGS. 3-6, for example, various embodiments of a therapeutic kit 200 will now be described in more detail. In this particular embodiment, the kit 200 includes a pad 202 that is formed from an extensible material 203 and is configured to wrap around the arm of a user. A base 210 is attached to the extensible material 203 that may be formed from a material that is flexible enough to allow normal functional movement of areas not associated with the specifically treated area, but that is sufficiently non-extensible to provide pressure, compression, and/or support to a treated area. For example, the base 210 may be formed from a soft polymeric material. The base 210 may be attached to the extensible material 203 in any manner desired, such as using stitches, adhesives, thermal bonds, etc. Loops 204A and 204B are also attached to the outer edges of the base 210. The extensible material 203 is capable of being inserted through the loops 204A and 204B to attach the pad 202 to a body part. Although not required, the loops 204A and 204B are typically formed from a hard polymeric material. The pad 202 also includes fasteners 208 and 214 (e.g., hook and loop, snaps, buttons, tape, etc.). The fasteners 208 and 214 may be brought together to inhibit loosening of the extensible material 203 during use. In this particular embodiment, the pad 202 also includes a receptacle 206 that is attached to the extensible material 203 and defines a cavity 217 for receiving a thermal insert 212 (FIG. 5). The cavity 217 may be formed by attaching three sides of the receptacle 206 to the extensible material 203 so that the thermal insert 212 is received through the fourth unattached side. The unattached side may have a fastener, such as snaps, buttons, hook and loop fasteners, etc., to help close and seal the cavity 217 upon receipt of the thermal insert 212. Although only one side is described as being unattached in this embodiment, it should be understood that one or more other sides may also be unattached for receiving the thermal insert 212. Such unattached side(s) likewise employ a fastener, such as described above.

To apply the pad 202 to a specified area, the end of the extensible material 203 located closest to the fastener 208 is wrapped around the desired area and fed through the loop 204A. This allows initial placement of the extensible material 203 and application of some pressure to the treated area. After passing through the loop 204A, the extensible material 203 is wrapped back under the area and fed through the loop 204B. By pulling the extensible material 203 through the loop 204B, the thermal insert 212 is pressed directly down on the desired area. Thereafter, the extensible material 203 is pulled tight and secured in place using fasteners 208 and 214.

The thermal insert of the present invention generally contains an exothermic coating that is capable of generating heat in the presence of moisture and oxygen. The exothermic coating may be formed from a variety of different components, including oxidizable metals, carbon components, binders, electrolytic salts, and so forth. Examples of such metals include, but are not limited to, iron, zinc, aluminum, magnesium, and so forth. Although not required, the metal may be initially provided in powder form to facilitate handling and to reduce costs. Various methods for removing impurities from a crude metal (e.g. iron) to form a powder include, for example, wet processing techniques, such as solvent extraction, ion exchange, and electrolytic refining for separation of metallic elements; hydrogen gas ($H_2$) processing for removal of gaseous elements, such as oxygen and nitrogen; floating zone melting refining method. Using such techniques, the metal purity may be at least about 95%, in some embodiments at least about 97%, and in some embodiments, at least about 99%. The particle size of the metal powder may also be less than about 500 micrometers, in some embodiments less than about 100 micrometers, and in some embodiments, less than about 50 micrometers. The use of such small particles may enhance the contact surface of the metal with air, thereby improving the likelihood and efficiency of the desired exothermal reaction. The concentration of the metal powder employed may generally vary depending on the nature of the metal powder, and the desired extent of the exothermal/oxidation reaction. In most embodiments, the metal powder is present in the exothermic coating in an amount from about 40 wt. % to about 95 wt. %, in some embodiments from about 50 wt. % to about 90 wt. %, and in some embodiments, from about 60 wt. % to about 80 wt. %.

In addition to an oxidizable metal, a carbon component may also be utilized in the exothermic coating of the present invention. Without intending to be limited in theory, it is believed that such a carbon component promotes the oxidation reaction of the metal and acts as a catalyst for generating heat. The carbon component may be activated carbon, carbon black, graphite, and so forth. When utilized, activated carbon may be formed from sawdust, wood, charcoal, peat, lignite, bituminous coal, coconut shells, etc. Some suitable forms of activated carbon and techniques for formation thereof are described in U.S. Pat. Nos. 5,693,385 to Parks; 5,834,114 to EconomV, et al.; 6,517,906 to Economy, et al.; 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes.

The exothermic coating may also employ a binder for enhancing the durability of the coating when applied to a substrate. The binder may also serve as an adhesive for bonding one substrate to another substrate. Generally speaking, any of a variety of binders may be used in the exothermic coating of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the latexes typically has a glass transition temperature of about 30° C. or less so that the flexibility of the resulting substrate is not substantially restricted. Moreover, the polymer also typically has a glass transition temperature of about −25° C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer latexes that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer latexes described above may be readily varied, as is well known in the art, by utilizing a stabilizing agent having the desired charge during preparation of the polymer latex. Specific techniques for a carbon/polymer latex system are described in more detail in U.S. Pat. No. 6,573,212 to McCrae, et al. Activated carbon/polymer latex systems that may be used in the present invention include Nuchar® PMA, DPX-8433-68A, and DPX-8433-68B, all of which are available from MeadWestvaco Corp of Stamford, Conn.

If desired, the polymer latex may be crosslinked using any known technique in the art, such as by heating, ionization, etc. Preferably, the polymer latex is self-crosslinking in that external crosslinking agents (e.g., N-methylol acrylamide) are not required to induce crosslinking. Specifically, crosslinking agents may lead to the formation of bonds between the polymer latex and the substrate to which it is applied. Such bonding may sometimes interfere with the effectiveness of the substrate in generating heat. Thus, the polymer latex may be substantially free of crosslinking agents. Particularly suitable self-crosslinking polymer latexes are ethylene-vinyl acetate copolymers available from Celanese Corp. of Dallas, Tex. under the designation DUR-O-SET® Elite (e.g., PE-25220A). Alternatively, an inhibitor may simply be employed that reduces the extent of crosslinking, such as free radical scavengers, methyl hydroquinone, t-butylcatechol, pH control agents (e.g., potassium hydroxide), etc.

Although polymer latexes may be effectively used as binders in the present invention, such compounds sometimes result in a reduction in drapability and an increase in residual odor. Thus, the present inventor has discovered that water-soluble organic polymers may also be employed as binders, either alone or in conjunction with the polymer latexes, to alleviate such concerns. For example, one class of water-soluble organic polymers found to be suitable in the present invention is polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is methylcellulose having a degree of methoxyl substitution (DS) of 1.8. The degree of methoxyl substitution represents the average number of hydroxyl groups present on each anhydroglucose unit that have been reacted, which may vary between 0 and 3. One such cellulosic ether is METOLOSE SM-100, which is a methylcellulose commercially available from Shin-Etsu Chemical Co., Ltd. Other suitable cellulosic ethers are also available from Hercules, Inc. of Wilmington, Del. under the name "CULMINAL."

The concentration of the carbon component and/or binder in the exothermic coating may generally vary based on the desired properties of the substrate. For example, the amount of the carbon component is generally tailored to facilitate the oxidation/exothermic reaction without adversely affecting other properties of the substrate. Typically, the carbon component is present in the exothermic coating in an amount about 0.01 wt. % to about 20 wt. %, in some embodiments from about 0.1 wt. % to about 15 wt. %, and in some embodiments, from about 1 wt. % to about 12 wt. %. In addition, although relatively high binder concentrations may provide better physical properties for the exothermic coating, they may likewise have an adverse effect on other properties, such as the absorptive capacity of the substrate to which it is applied. Conversely, relatively low binder concentrations may reduce the ability of the exothermic coating to remain affixed on the substrate. Thus, in most embodiments, the binder is present in the exothermic coating in an amount from about 0.01 wt. % to about 20 wt. %, in some embodiments from about 0.1 wt. % to about 10 wt. %, and in some embodiments, from about 0.5 wt. % to about 8 wt. %.

Still other components may also be employed in the exothermic coating of the present invention. For example, as is well known in the art, an electrolytic salt may be employed to react with and remove any passivating oxide layer(s) that might otherwise prevent the metal from oxidizing. Suitable electrolytic salts may include, but are not limited to, alkali halides or sulfates, such as sodium chloride, potassium chloride, etc.; alkaline halides or sulfates, such as calcium chloride, magnesium chloride, etc., and so forth. When employed, the electrolytic salt is typically present in the exothermic coating in an amount from about 0.01 wt. % to about 10 wt. %, in some embodiments from about 0.1 wt. % to about 8 wt. %, and in some embodiments, from about 1 wt. % to about 6 wt. %.

In addition, particles may also be employed in the exothermic coating that act as moisture retainers. That is, prior to the oxidation/exothermic reaction, these particles may retain moisture. However, after the reaction has proceeded to a certain extent and the moisture concentration is reduced, the particles may release the moisture to allow the reaction to continue. Besides acting as a moisture retainer, the particles may also provide other benefits to the exothermic coating of the present invention. For example, the particles may alter the black color normally associated with the carbon component and/or metal powder. When utilized, the size of the moisture-retaining particles may be less than about 500 micrometers, in some embodiments less than about 100 micrometers, and in some embodiments, less than about 50 micrometers. Likewise, the particles may be porous. Without intending to be limited by theory, it is believed that porous particles may provide a passage for air and/or water vapors to better contact the metal powder. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to retain moisture and also to alter the black color normally associated with activated carbon and/or metal powder. Such a color change may be more aesthetically pleasing to a user, particularly when the coating is employed on substrates designed for consumer/personal use. Suitable white calcium carbonate particles are commercially available in both dry and aqueous slurry form from Omya, Inc. of Proctor, Vt. Still other suitable inorganic particles that may retain moisture include, but are not limited to, silicates, such as calcium silicate, alumina silicates (e.g., mica powder, clay, etc.), magnesium silicates (e.g., talc), quartzite, calcium silicate fluorite, vermiculite, etc.; alumina; silica; and so forth. The concentration of the particles may generally vary depending on the nature of the particles, and the desired extent of exothermic reaction and color alteration. For instance, the particles may be present in the exothermic coating in an amount from about 0.01 wt. % to about 30 wt. %, in some embodiments from about 0.1 wt. % to about 20 wt. %, and in some embodiments, from about 1 wt. % to about 15 wt. %.

In addition to the above-mentioned components, other components, such as surfactants, pH adjusters, dyes/pigments/inks, viscosity modifiers, etc., may also be included in the exothermic coating of the present invention. Viscosity modifiers may be used, for example, to adjust the viscosity of the coating formulation based on the desired coating process and/or performance of the coated substrate. Suitable viscosity modifiers may include gums, such as xanthan gum. Binders, such as the cellulosic ethers, may also function as suitable viscosity modifiers. When employed, such additional components typically constitute less than about 5 wt. %, in some embodiments less than about 2 wt. %, and in some embodiments, from about 0.001 wt. % to about 1 wt. % of the exothermic coating.

Regardless of the manner in which it is formed, the exothermic coating is applied to a substrate, which may perform other functions of the thermal insert or simply act as a physical carrier for the coating. Any type of substrate may be applied with the exothermic coating in accordance with the present invention. For instance, nonwoven webs, woven fabrics, knit fabrics, paper webs, films, foams, etc., may be applied with the exothermic coating. Typically, the polymers used to form the substrate have a softening or melting temperature that is higher than the temperature needed to evaporate moisture. One or more components of such polymers may have, for instance, a softening temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR™, syndiotactic polystyrene, liquid crystalline polyesters, etc.); cellulosic polymers (softwood pulp, hardwood pulp, thermomechanical pulp, etc.); combinations thereof; and so forth.

To apply the exothermic coating of the present invention to a substrate, the components may initially be dissolved or dispersed in a solvent. For example, one or more of the above-mentioned components may be mixed with a solvent, either sequentially or simultaneously, to form a coating formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. The concentration of the solvent is generally high enough to inhibit oxidization of the metal prior to use. Specifically, when present in a high enough concentration, the solvent may act as a barrier to prevent air from prematurely contacting the oxidizable metal. If the amount of solvent is too small, however, the exothermic reaction may occur prematurely. Likewise, if the amount of solvent is too large, the amount of metal deposited on the substrate might be too low to provide the desired exothermal effect. Although the actual concentration of solvent (e.g., water) employed will generally depend on the type of oxidizable metal and the substrate on which it is applied, it is nonetheless typically present in an amount from about 10 wt. % to about 80 wt. %, in some embodiments from about 20 wt. % to about 70 wt. %, and in some embodiments, from about 25 wt. % to about 60 wt. % of the coating formulation.

The amount of the other components added to the coating formulation may vary depending on the amount of heat desired, the wet pick-up of the application method utilized, etc. For example, the amount of the oxidizable metal (in powder form) within the coating formulation generally ranges from about 20 wt. % to about 80 wt. %, in some embodiments from about 30 wt. % to about 70 wt. %, and in some embodiments, from about 35 wt. % to about 60 wt. %. In addition, the carbon component may constitute from about 0.1 wt. % to about 20 wt. %, in some embodiments from about 0.1 wt. % to about 15 wt. %, and in some embodiments, from about 0.2 wt. % to about 10 wt. %. of the coating formulation. Binders may constitute from about 0.01 wt. % to about 20 wt. %, in some embodiments from about 0.1 wt. % to about 15 wt. %, and in some embodiments, from about 1 wt. % to about 10 wt. % of the coating formulation. Electrolytic salts may constitute from about 0.01 wt. % to about 10 wt. %, in some embodiments from about 0.1 wt. % to about 8 wt. %, and in some embodiments, from about 1 wt. % to about 5 wt. %. of the coating formulation. Further, moisture-retaining particles (e.g., calcium carbonate) may constitute from about 2 wt. % to about 30 wt. %, in some embodiments from about 3 wt. % to about 25 wt. %, and in some embodiments, from about 4 wt. % to about 10 wt. %. of the coating formulation. Other components, such as surfactants, pH adjusters, viscosity modifiers, etc., may also constitute from about 0.001 wt. % to about 5 wt. %, in some embodiments from about 0.01 wt. % to about 1 wt. %, and in some embodiments from about 0.02 wt. % to about 0.5 wt. % of the coating formulation.

The solids content and/or viscosity of the coating formulation may be varied to achieve the desired amount of heat generation. For example, the coating formulation may have a solids content of from about 30% to about 80%, in some embodiments from about 40% to about 70%, and in some embodiments, from about 50% to about 60%. By varying the solids content of the coating formulation, the presence of the metal powder and other components in the exothermic coating may be controlled. For example, to form an exothermic coating with a higher level of metal powder, the coating formulation may be provided with a relatively high solids content so that a greater percentage of the metal powder is incorporated into the exothermic coating during the application process. In addition, the viscosity of the coating formulation may also vary depending on the coating method and/or type of binder employed. For instance, lower viscosities may be employed for saturation coating techniques (e.g., dip-coating), while higher viscosities may be employed for drop-coating techniques. Generally, the viscosity is less than about $2 \times 10^6$ centipoise, in some embodiments less than about $2 \times 10^5$ centipoise, in some embodiments less than about $2 \times 10^4$ centipoise, and in some embodiments, less than about $2 \times 10^3$ centipoise, such as measured with a Brookfield DV-1 viscometer with an LV spindle. If desired, thickeners or other viscosity modifiers may be employed in the coating formulation to increase or decrease viscosity.

The coating formulation may be applied to a substrate using any conventional technique, such as bar, roll, knife, curtain, print (e.g., rotogravure), spray, slot-die, drop-coating, or dip-coating techniques. The materials that form the substrate (e.g., fibers) may be coated before and/or after incorporation into the substrate. The coating may be applied to one or both surfaces of the substrate. For example, the exothermic coating may be present on a surface of the substrate that is opposite to that facing the wearer or user to avoid the possibility of burning. In addition, the coating formulation may cover an entire surface of the substrate, or may only cover a portion of the surface. When applying the exothermic coating to multiple surfaces, each surface may be coated sequentially or simultaneously.

Regardless of the manner in which the coating is applied, the resulting substrate is typically heated to a certain temperature to remove the solvent and any moisture from the coating. For example, the substrate may be heated to a temperature of at least about 100° C., in some embodiments at least about 110° C., and in some embodiments, at least about 120° C. In this manner, the resulting dried exothermic coating is anhydrous, i.e., generally free of water. By minimizing the amount of moisture, the exothermic coating is less likely to react prematurely and generate heat. That is, the oxidizable metal does not generally react with oxygen unless some minimum amount of water is present. Thus, the exothermic coating may remain inactive until placed in the vicinity of moisture (e.g., next to a layer that contains moisture) during use. It should be understood, however, that relatively small amounts of water may still be present in the exothermic coating without causing a substantial exothermic reaction. In some embodiments, for example, the exothermic coating contains water in an amount less than about 0.5% by weight, in some embodiments less than about 0.1% by weight, and in some embodiments, less than about 0.01% by weight.

The solids add-on level of the exothermic coating may also be varied as desired. The "solids add-on level" is determined by subtracting the weight of the untreated substrate from the weight of the treated substrate (after drying), dividing this calculated weight by the weight of the untreated substrate, and then multiplying by 100%. Lower add-on levels may optimize certain properties (e.g., absorbency), while higher add-on levels may optimize heat generation. In some embodiments, for example, the add-on level is from about 100% to about 5000%, in some embodiments from about 200% to about 2400%, and in some embodiments, from about 400% to about 1200%. The thickness of the exothermic coating may also vary. For example, the thickness may range from about 0.01 millimeters to about 5 millimeters, in some embodiments, from about 0.01 millimeters to about 3 millimeters, and in some embodiments, from about 0.1 millimeters to about 2 millimeters. In some cases, a relatively thin coating may be employed (e.g., from about 0.01 millimeters to about 0.5 millimeters). Such a thin coating may enhance the flexibility of the substrate, while still providing uniform heating.

To maintain porosity, flexibility, and/or some other characteristic of the substrate, it may sometimes be desired to apply the exothermic coating so as to cover less than 100%, in some embodiments from about 10% to about 80%, and in some embodiments, from about 20% to about 60% of the area of one or more surfaces of the substrate. For instance, in one particular embodiment, the exothermic coating is applied to the substrate in a preselected pattern (e.g., reticular pattern, diamond-shaped grid, dots, and so forth). Although not required, such a patterned exothermic coating may provide sufficient warming to the substrate without covering a substantial portion of the surface area of the substrate. This may be desired to optimize flexibility, absorbency, or other characteristics of the substrate. It should be understood, however, that the coating may also be applied uniformly to one or more surfaces of the substrate. In addition, a patterned exothermic coating may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first exothermic coating, while another region is coated with a second exothermic coating. If desired, one region may provide a different amount of heat than another region.

Besides having functional benefits, the substrate may also have various aesthetic benefits as well. For example, although containing activated carbon, the substrate may be made without the black color commonly associated with activated carbon. In one embodiment, white or light-colored particles (e.g., calcium carbonate, titanium dioxide, etc.) are employed in the exothermic coating so that the resulting substrate has a grayish or bluish color. In addition, various pigments, dyes, and/or inks may be employed to alter the color of the exothermic coating. The substrate may also be applied with patterned regions of the exothermic coating to form a substrate having differently colored regions.

Other substrates may also be employed to improve the exothermic properties of the substrate. For example, a first substrate may be employed in conjunction with a second substrate. The substrates may function together to provide heat to a surface, or may each provide heat to different surfaces. In addition, substrates may be employed that are not applied with the exothermic coating of the present invention, but instead applied with a coating that simply facilitates the reactivity of the exothermic coating. For example, a substrate may be used near or adjacent to the substrate of the present invention that includes a coating of moisture-retaining particles. As described above, the moisture-retaining particles may retain and release moisture for activating the exothermic reaction.

As indicated above, moisture and oxygen are supplied to the exothermic coating to activate the exothermic reaction. To provide the desired heating profile, the rate at which moisture is allowed to contact the exothermic coating may be selectively controlled in accordance with the present invention. Namely, if too much moisture is supplied within a given time period, the exothermic reaction may produce an excessive amount of heat that overly warms or burns the user. On the other hand, if too little moisture is supplied within a given time period, the exothermic reaction may not be sufficiently activated. The desired application rate may of course be achieved by manually applying the desired amount of moisture, e.g., by hand or with the aid of external equipment, such as a syringe. Alternatively, the thermal insert itself may contain a mechanism for controlling the moisture release rate.

One technique for using the thermal insert as a mechanism for controlling the moisture application rate involves the use of a moisture-holding layer. The moisture-holding layer may be employed in the thermal insert to hold moisture and controllably release it to the exothermic coating over an extended period of time. The moisture-holding layer may include an absorbent web formed according to any conventional method or technique, such a dry-forming technique, an airlaying technique, a carding technique, a meltblown or spunbond technique, a wet-forming technique, a foam-forming technique, etc. In an airlaying process, for example, bundles of small fibers having typical lengths ranging from about 3 to about 19 millimeters are separated and entrained in an air supply and then deposited onto a forming screen, usually with the assistance of a vacuum supply. The randomly deposited fibers then are bonded to one another using, for example, hot air or an adhesive.

The moisture-holding layer typically contains cellulosic fibers, such as natural and/or synthetic fluff pulp fibers. The fluff pulp fibers may be kraft pulp, sulfite pulp, thermomechanical pulp, etc. In addition, the fluff pulp fibers may include high-average fiber length pulp, low-average fiber length pulp, or mixtures of the same. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and so forth. Northern softwood kraft pulp fibers may be used in the present invention. One example of commercially available southern softwood kraft pulp fibers suitable for use in the present invention include those available from Weyerhaeuser Company with offices in Federal Way, Wash. under the trade designation of "NB-416." Another type of fluff pulp that may be used in the present invention is identified with the trade designation CR1654, available from U.S. Alliance of Childersburg, Ala., and is a bleached, highly absorbent sulfate wood pulp containing primarily softwood fibers. Still another suitable fluff pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability.

If desired, the moisture-holding layer may also contain synthetic fibers, such as monocomponent and multicomponent (e.g., bicomponent) fibers. Multicomponent fibers, for instance, are fibers formed from at least two thermoplastic polymers that are extruded from separate extruders, but spun together to form one fiber. In a sheath/core multicomponent fiber, a first polymer component is surrounded by a second polymer component. The polymers of the multicomponent fibers are arranged in substantially constantly positioned distinct zones across the cross-section of the fiber and extend continuously along the length of the fibers. Various combinations of polymers for the multicomponent fiber may be useful in the present invention, but the first polymer component typically melts at a temperature lower than the melting temperature of the second polymer component. Melting of the first polymer component allows the fibers to form a tacky skeletal structure, which upon cooling, captures and binds many of the pulp fibers. Typically, the polymers of the multicomponent fibers are made up of different thermoplastic materials, such as polyolefin/polyester (sheath/core) bicomponent fibers in which the polyolefin (e.g., polyethylene sheath) melts at a temperature lower than the core (e.g., polyester). Exemplary thermoplastic polymers include polyolefins (e.g. polyethylene, polypropylene, polybutylene, and copolymers thereof), polytetrafluoroethylene, polyesters (e.g. polyethylene terephthalate), polyvinyl acetate, polyvinyl chloride acetate, polyvinyl butyral, acrylic resins (e.g. polyacrylate, polymethylacrylate, and polymethylmethacrylate), polyamides (e.g., nylon), polyvinyl chloride, polyvinylidene chloride, polystyrene, polyvinyl alcohol, polyurethanes, cellulosic resins (e.g., cellulosic nitrate, cellulosic acetate, cellulosic acetate butyrate, and ethyl cellulose), and copolymers of any of the above materials, such as ethylene-vinyl acetate copolymers, ethylene-acrylic acid copolymers, styrene-butadiene block copolymers, and so forth.

The moisture-holding layer may also include a superabsorbent material, such as natural, synthetic and modified natural materials. Superabsorbent materials are water-swellable materials capable of absorbing at least about 20 times its weight and, in some cases, at least about 30 times its weight in an aqueous solution containing 0.9 weight percent sodium chloride. Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Other suitable absorbent gelling materials are disclosed in U.S. Pat. Nos. 3,901,236 to Assarsson et al.; 4,076,663 to Masuda et al.; and 4,286,082 to Tsubakimoto et al., which are incorporated herein in their entirety by reference thereto for all purposes.

When utilized, the superabsorbent material may constitute from about 1 wt. % to about 40 wt. %, in some embodiments, from about 5 wt. % to about 30 wt. %, and in some embodiments, from about 10 wt. % to about 25 wt. % of the moisture-holding layer (on a dry basis). Likewise, multicomponent fibers may constitute from about 1 wt. % to about 30 wt. %, in some embodiments, from about 2 wt. % to about 20 wt. %, and in some embodiments, from about 5 wt. % to about 15 wt. % of the moisture-holding layer (on a dry basis). The cellulosic fibers may also constitute up to 100 wt. %, in some embodiments from about 50 wt. % to about 95 wt. %, and in some embodiments, from about 65 wt. % to about 85 wt. % of the moisture-holding layer (on a dry basis).

In accordance with the present invention, it has been discovered that the nature of the moisture-holding layer may be selected to provide a controlled evaporation rate of moisture from the moisture-holding layer. By controlling the evaporation rate, the desired amount of moisture may be released to the exothermic coating within a given period of time. For example, it is normally desired that the average "evaporation rate" of moisture from the moisture-holding layer is from about 0.05% to about 0.5%, in some embodiments from about 0.10% to about 0.25%, and in some embodiments, from about 0.15% to about 0.20% per minute. The "evaporation rate" is determined by measuring the weight of moisture-holding layer at a certain time, subtracting this measured weight from the initial wet weight of the layer, dividing this value by the initial wet weight, and then multiplying by 100. The evaporation rates are calculated for several different times and then averaged. The evaporation rate is determined in the present invention at a relative humidity of 51% and temperature of about 22° C. It should be understood that these relative humidity and temperature conditions are "initial" conditions in that they may vary during testing due to the increased presence of water vapor in the atmosphere.

In some embodiments, the desired evaporation rate of moisture is achieved by controlling the nature of the aqueous solution applied to the moisture-holding layer. Namely, the present inventor has discovered that the application of only water (vapor pressure of 23.7 mm Hg at 25° C.) to the moisture-holding layer may sometimes result in too great of an evaporation rate. Thus, a solute may be added to the aqueous solution to reduce its vapor pressure, i.e., the tendency of the water molecules to evaporate. At 25° C., for example, the solute may be added so that the aqueous solution added to the moisture-holding layer has an evaporation rate of less than 23.7 mm Hg, in some embodiments less than about 23.2 mm Hg, and in some embodiments, from about 20.0 mm Hg to about 23.0 mm Hg. One particularly suitable class of solutes includes organic and/or inorganic metal salts. The metal salts may contain monovalent (e.g., $Na^+$), divalent (e.g., $Ca^{2+}$), and/or polyvalent cations. Examples of preferred metal cations include the cations of sodium, potassium, calcium, aluminum, iron, magnesium, zirconium, zinc, and so forth. Examples of preferred anions include halides, chlorohydrates, sulfates, citrates, nitrates, acetates, and so forth. Particular examples of suitable metal salts include sodium chloride, sodium bromide, potassium chloride, potassium bromide, calcium chloride, etc. The actual concentration of the solute in the aqueous solution may vary depending on the nature of the solute, the particular configuration of the thermal insert, and the desired heating profile. For example, the solute may be present in the aqueous solution in an amount from about 0.1 wt. % to about 25 wt. %, in some embodiments from about 1 wt. % to about 20 wt. %, and in some embodiments, from about 5 wt. % to about 15 wt. % of the solution.

In addition to controlling aspects of the aqueous solution, the moisture-holding layer itself may be selectively tailored to achieve the desired evaporation rate. For example, the present inventor has discovered that moisture-holding layers having a relatively low density and basis weight tend to release too great an amount of moisture in comparison to those having a higher density and basis weight. Without intending to be limited by theory, it is believed that such high density and high basis weight webs may have a lower porosity, thereby making it more difficult for moisture to escape from the layer over an extended period of time. Thus, in one embodiment of the present invention, the moisture-holding layer (e.g., airlaid web) may have a density of from about 0.01 to about 0.50, in some embodiments from about 0.05 to about 0.25, and in some embodiments, from about 0.05 to about 0.15 grams per cubic centimeters (g/cm$^3$). The density is based on the oven-dry mass of the sample and a thickness measurement made at a load of 0.34 kilopascals (kPa) with a 7.62-cm diameter circular platen at 50% relative humidity and 23° C. In addition, the basis weight of the moisture-holding layer may be from about 50 to about 500 grams per square meter ("gsm"), in some embodiments from about 100 to about 300 gsm, and in some embodiments, from about 150 to about 300 gsm.

Other techniques may also be employed to achieve the desired evaporation rate of moisture from the moisture-holding layer. For example, superabsorbent materials are capable of swelling in the presence of an aqueous solution. Swelling increases the absorption capacity of the moisture-holding layer, but likewise reduces the evaporation rate of moisture as the materials exhibit a greater tendency to "hold onto" the water molecules. Thus, the evaporation rate may be increased by reducing the degree of swelling. One technique for reducing the degree of swelling of a superabsorbent material involves reducing the temperature of the aqueous solution to below ambient temperature, such as less than about 25° C., and in some embodiments, from about 5° C. to about 20° C. The degree of swelling of the superabsorbent material may also be reduced by incorporating one or more ionic compounds into the aqueous solution to increase its ionic strength. The ionic compounds may be the same as the solutes described above. The "ionic strength" of a solution may be determined according to the following equation:

$$I=0.5*\Sigma z_i^2 * m_i$$

wherein, $z_i$ the valence factor; and $m_i$ is the concentration. For example, the ionic strength of a solution containing 1 molar calcium chloride and 2 molar sodium chloride is "3" and determined as follows:

$$I=0.5*[(2^2*1)+(1^2*2)]=3$$

Without intending to be limited by theory, it is believed that superabsorbent materials have a counterion atmosphere surrounding the ionic backbone of the polymer chains that collapses when its ionic strength is increased. Specifically, the counterion atmosphere is made up of ions of opposite charge to the charges along the backbone of a superabsorbent polymer and are present in the ionic compound (e.g., sodium or potassium cations surrounding the carboxylate anions distributed along the backbone of a polyacrylate anionic polymer). As the concentration of ions contacting the superabsorbent polymer increases, the ion concentration gradient in the liquid phase from the exterior to the interior of the polymer begins to decrease and the counterion atmosphere thickness ("Debye thickness") may be reduced from about 20 nanometers (in pure water) to about 1 nanometer or less. When the counterion atmosphere is highly extended, the counterions are more osmotically active and therefore promote a higher degree of liquid absorbency. To the contrary, when the ion concentration in the absorbed liquid increases, the counterion atmosphere collapses and the absorption capacity is diminished. As a result of the reduction in absorption capacity, the superabsorbent material exhibits less of a tendency to hold the water molecules, thereby allowing its release to the exothermic composition.

If desired, a breathable layer may also be employed that permits the flow of water vapor and air for activating the exothermic reaction, but prevents an excessive amount of liquids from contacting the substrate, which could either suppress the reaction or result in an excessive amount of heat that overly warms or burns the user. The breathable layer may contain a breathable film. One suitable breathable film is a microporous film. The micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. Nos. 5,843,057 to McCormack; 5,855,999 to McCormack; 5,932,497 to Morman, at al.; 5,997,981 to McCormack et al.; 6,002,064 to Kobylivker, et al.; 6,015,764 to McCormack, et al.; 6,037,281 to Mathis, et al.; 6,111,163 to McCormack, et al.; and 6,461,457 to Taylor, et al., which are incorporated herein in their entirety by reference thereto for all purposes.

The films are generally made breathable by stretching the filled films to create the microporous passageways as the polymer breaks away from the filler (e.g., calcium carbonate) during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

Breathable films, such as described above, may constitute the entire breathable material, or may be part of a multilayer film. Multilayer films may be prepared by cast or blown film coextrusion of the layers, by extrusion coating, or by any conventional layering process. Further, other breathable materials that may be suitable for use in the present invention are described in U.S. Pat. Nos. 4,341,216 to Obenour; 4,758,239 to Yeo, et al.; 5,628,737 to Dobrin, et al.; 5,836,932 to Buell; 6,114,024 to Forte; 6,153,209 to Vega, et al.; 6,198,018 to Curro; 6,203,810 to Alemany, et al.; and 6,245,401 to Ying, et al., which are incorporated herein in their entirety by reference thereto for all purposes.

If desired, the breathable film may also be bonded to a nonwoven web, knitted fabric, and/or woven fabric using well-known techniques. For instance, suitable techniques for bonding a film to a nonwoven web are described in U.S. Pat. Nos. 5,843,057 to McCormack; 5,855,999 to McCormack; 6,002,064 to Kobylivker, et al.; 6,037,281 to Mathis, et al.; and WO 99/12734, which are incorporated herein in their entirety by reference thereto for all purposes. For example, a breathable film/nonwoven laminate material may be formed from a nonwoven layer and a breathable film layer. The layers may be arranged so that the breathable film layer is attached to the nonwoven layer. In one particular embodiment, the breathable material is formed from a nonwoven fabric (e.g., polypropylene spunbonded web) laminated to a breathable film.

Although various configurations of a thermal insert have been described above, it should be understood that other configurations are also included within the scope of the present invention. For instance, other layers may also be employed to improve the exothermic properties of the thermal insert. For example, a substrate may be used near or adjacent to the substrate of the present invention that includes a coating of moisture-retaining particles. As described above, the moisture-retaining particles may retain and release moisture for activating the exothermic reaction. Furthermore, of particular benefit, one or more of the above-mentioned layers may accomplish multiple functions of the thermal insert. For example, in some embodiments, the breathable layer, moisture-holding layer, etc., may be applied with an exothermic coating and thus also serve as a substrate. Although not expressly set forth herein, it should be understood that numerous other possible combinations and configurations would be well within the ordinary skill of those in the art.

The above-described moisture-holding and/or breathable layers may generally be arranged in any desired position relative to the exothermic coating. In this regard, various configurations of the thermal insert of the present invention will now be described in more detail. It should be understood, however, that the description below is merely exemplary, and that other thermal insert configurations are also contemplated by the present inventor.

Referring to FIG. 1 for example, one embodiment of a thermal insert 10 that may be formed in accordance with the present invention is shown. As shown, the thermal insert 10 defines two outer surfaces 17 and 19, and is in the form of a substantially flat, conformable, and foldable material. The overall size and shape of the thermal insert 10 are not critical. For example, the thermal insert 10 may have a shape that is generally triangular, square, rectangular, pentagonal, hexagonal, circular, elliptical, etc. As shown, the thermal insert 10 includes a substrate 12 that contains one or more exothermic coatings. In this embodiment, breathable layers 14a and 14b are included within the thermal insert 10 that are impermeable to liquids, but permeable to gases. It should be understood that, although shown herein as having two breathable layers, any number of breathable layers (if any) may be employed in the present invention. The thermal insert 10 also includes a moisture-holding layer 16 that is configured to absorb and hold moisture for an extended period of time. The breathable layers 14a and 14b and the moisture-holding layer 16 may be positioned in various ways relative to the substrate 12. In FIG. 1, for example, the breathable layers 14a and 14b are positioned directly adjacent to the substrate 12. As a result, the breathable layers 14a and 14b may prevent external liquids from contacting the substrate 12 and may also control the amount of air that contacts the substrate 12 over a given period of time. The moisture-holding layer 16 may also be positioned in various locations, but is generally positioned to help facilitate the source of moisture for the substrate 12. It should be understood that, although shown herein as having one moisture-holding layer, any number of layers (if any) may be employed in the present invention.

Although not specifically illustrated, the thermal insert 10 may also include various other layers. For example, the thermal insert 10 may employ a thermally conductive layer to help distribute heat toward the direction of a user (i.e., −z direction) and/or along the x-y plane of the device 10, thereby improving the uniformity of heat application over a selected area. The thermally conductive layer may have a coefficient of thermal conductivity of at least about 0.1 Watts per meter-Kelvin (W/m-K), and in some embodiments, from about 0.1 to about 10 W/m-k. Although any thermally conductive material may generally be employed, it is often desired that the selected material be conformable to enhance the comfort and flexibility of the device 10. Suitable conformable materials include, for instance, fibrous materials (e.g., nonwoven webs), films, and so forth. Optionally, the thermally conductive layer may be vapor-permeable so that air may contact the substrate 12 when desired to activate the exothermic reaction. One type of vapor-permeable, conformable material that may be used in the thermally conductive layer is a nonwoven web material. For example, the thermally conductive layer may contain a nonwoven laminate, such as a spunbonded/meltblown/spunbonded ("SMS") laminate. Such SMS laminates may also provide liquid strike-through protection and breathability. The SMS laminate is formed by well-known methods, such as described in U.S. Pat. No. 5,213,881 to Timmons, et al., which is incorporated herein its entirety by reference thereto for all purposes. Another type of vapor-permeable, conformable material that may be used in the thermally conductive layer is a breathable film. For example, the thermally conductive layer may sometimes utilize a breathable film/nonwoven laminate.

A variety of techniques may be employed to provide conductivity to the thermally conductive layer. For example, a metallic coating may be utilized to provide conductivity. Metals suitable for such a purpose include, but are not limited to, copper, silver, nickel, zinc, tin, palladium, lead, copper, aluminum, molybdenum, titanium, iron, and so forth. Metallic coatings may be formed on a material using any of a variety of known techniques, such as vacuum evaporation, electrolytic plating, etc. For instance, U.S. Pat. Nos. 5,656,355 to Cohen; 5,599,585 to Cohen; 5,562,994 to Abba, et al.; and 5,316,837 to Cohen, which are incorporated herein their entirety by reference thereto for all purposes, describes suitable techniques for depositing a metal coating onto a material. Besides a metal coating, still other techniques may be employed to provide conductivity. For example, an additive may be incorporated into the material (e.g., fibers, film, etc.) to enhance conductivity. Examples of such additives include, but are not limited to, carbon fillers, such as carbon fibers and powders; metallic fillers, such as copper powder, steel, aluminum powder, and aluminum flakes; and ceramic fillers, such as boron nitride, aluminum nitride, and aluminum oxide. Commercially available examples of suitable conductive materials include, for instance, thermally conductive compounds available from LNP Engineering Plastics, Inc. of Exton, Pa. under the name Konduit® or from Cool Polymers of Warwick, R.I. under the name CoolPoly®. Although several examples of thermally conductive materials have been described above, it should be understood that any known thermally conductive material may be generally used in the present invention.

In addition to a thermally conductive layer, still other optional layers may be employed to enhance the effectiveness of the thermal insert 10. For example, an insulation layer may be employed to inhibit heat dissipation to the outer environment so that heat is instead focused toward the patient or user. Because the insulation layer increases the overall heat-producing efficiency of the device 10, the desired temperature increase may be reached with a lower amount of exothermic coating or other reactant (i.e., moisture or oxygen). The insulation layer may have a coefficient of thermal conductivity of less than about 0.1 Watts per meter-Kelvin (W/m-K), and in some embodiments, from about 0.01 to about 0.05 W/m-k. Any known insulation material may be employed in the present invention. If desired, the selected insulation material may be fibrous in nature to improve the overall conformability of the thermal insert 10. The fibrous material may possess high loft to enhance its insulative properties. Suitable high loft materials may include porous woven materials, porous nonwoven materials, etc. Particularly suitable high loft materials are nonwoven multicomponent (e.g., bicomponent) polymeric webs. For example, the multicomponent polymers of such webs may be mechanically or chemically crimped to increase loft. Examples of suitable high loft materials are described in more detail in U.S. Pat. Nos. 5,382,400 to Pike, et al.; 5,418,945 to Pike, et al. and 5,906,879 to Huntoon, et al., which are incorporated herein in their entirety by reference thereto for all purposes. Still other suitable materials for use as an insulation material are described in U.S. Pat. No. 6,197,045 to Carson, which is incorporated herein in its entirety by reference thereto for all purposes.

The thermal insert 10 may also include layers that optionally form the outer surfaces 17 and 19, respectively, of the thermal insert 10. These layers may present a compliant, soft feeling, and non-irritating surface to the user's skin. For example, the layers may be formed from materials that are liquid- and vapor-permeable, liquid-impermeable and vapor-permeable ("breathable"), and so forth. For example, the layers may be formed from a meltblown or spunbonded web of polyolefin fibers, as well as a bonded-carded, staple fiber, and/or hydraulically entangled web of natural and/or synthetic fibers. In another embodiment, the layers may be formed from a breathable nonwoven laminate (e.g., spunbond web/breathable film laminate), such as described above. The layers may further include a composition that is configured to transfer to the wearer's skin for improving skin health. Suitable compositions are described in U.S. Pat. No. 6,149,934 to Krzysik et al., which is incorporated herein in its entirety by reference thereto for all purposes.

The various layers and/or components of the thermal insert 10 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In some embodiments, the exothermic coating may serve the dual purposes of generating heat and also acting as the adhesive. For example, the binder of the exothermic coating may bond together one or more layers of the thermal insert 10.

Figure 2:
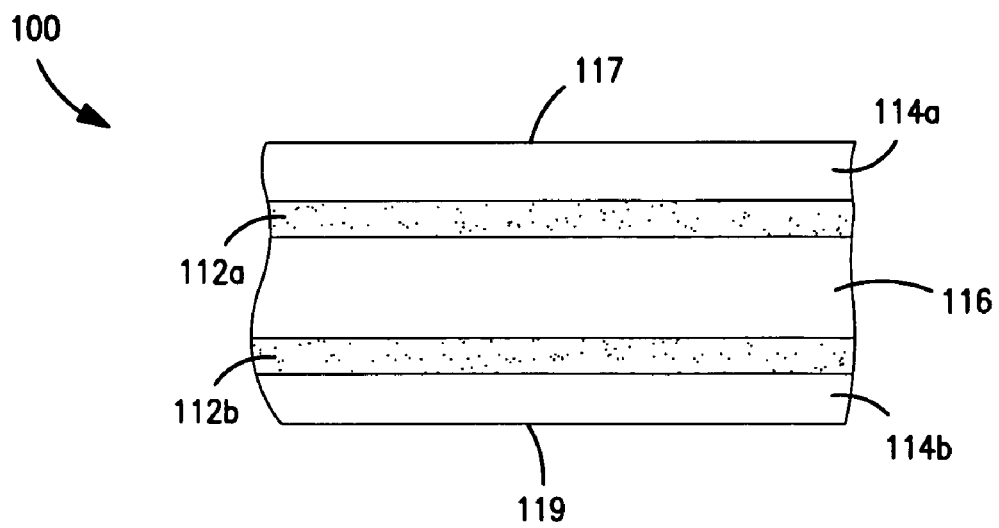
FIG. 2 illustrates a cross-sectional view of another embodiment of a thermal insert of the present invention.
Figure 6:
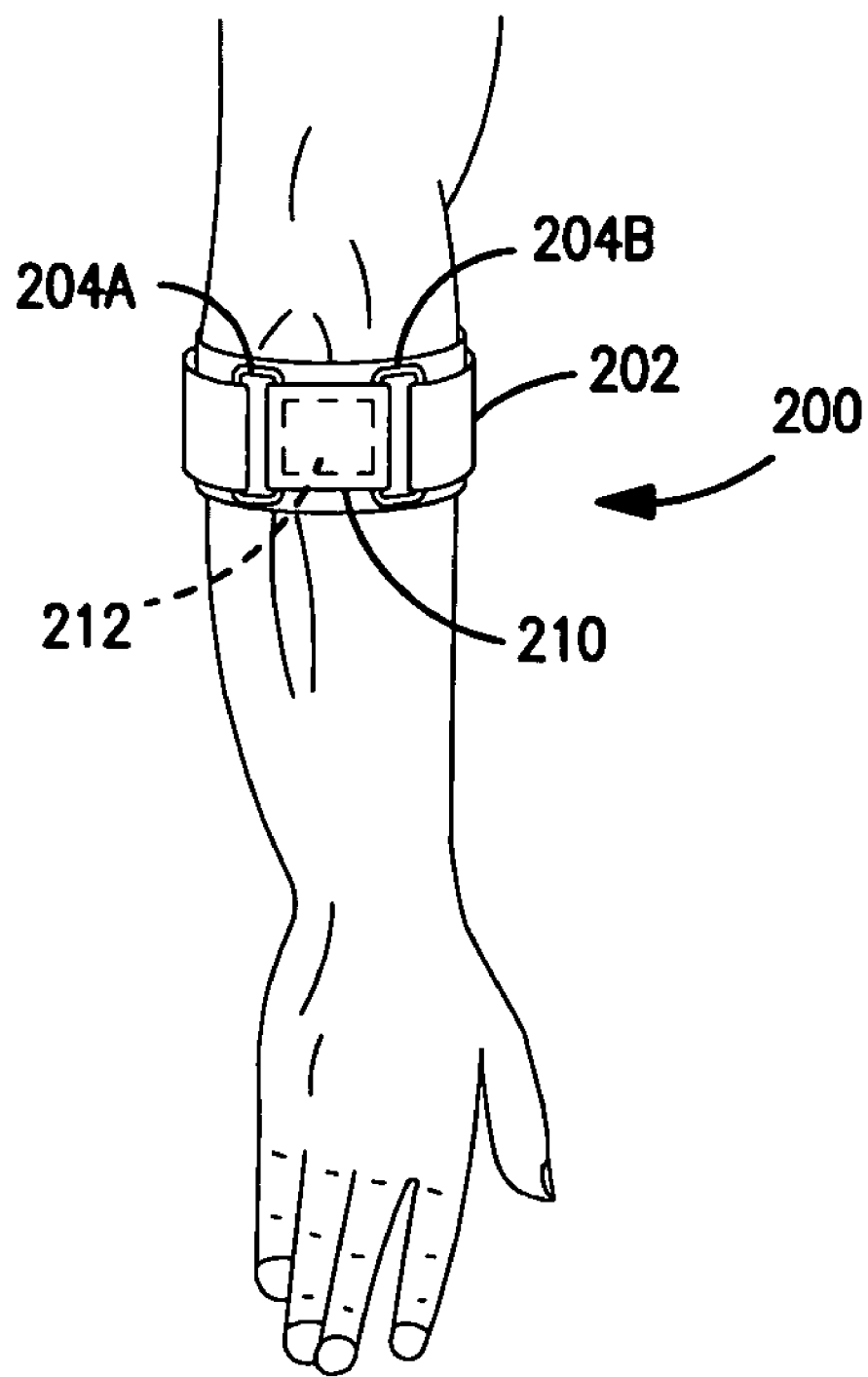
FIG. 6 is a perspective view of the pad of FIG. 3 positioned onto an arm.

To further enhance the amount of heat generated by the thermal insert, multiple substrates may sometimes be employed. The multiple substrates may be placed adjacent to one another or spaced apart by one or more layers. For example, referring to FIG. 2, one embodiment of a thermal insert 100 is shown that contains a first substrate 112a and a second substrate 112b. Although not required, the thermal insert 100 also includes a first breathable layer 114a and a second breathable layer 114b. The thermal insert 100 also includes a moisture-holding layer 116 for facilitating the supply of moisture to the substrates 112a and 112b. The moisture-holding layer 116 is positioned between the substrate 112a/breathable layer 114a and the substrate 112b/breathable layer 114b. In this manner, the amount of moisture supplied to each substrate is relatively uniform. It should be understood, however, that any placement, selection, and/or number of layers may be employed in the present invention.

Moisture may be applied any time prior to or during use of the thermal insert, such as just prior to use or during manufacture. For example, water may be pre-applied to the moisture-holding layer as described above. The moisture is added in an amount effective to activate an exothermic, electrochemical reaction between the electrochemically oxidizable element (e.g., metal powder) and the electrochemically reducible element (e.g., oxygen). Although this amount may vary depending on the reaction conditions and the amount of heat desired, the moisture is typically added in an amount from about 20 wt. % to about 500 wt. %, and in some embodiments, from about 50 wt. % to about 200 wt. %, of the weight of the amount of oxidizable metal present in the coating. Although not necessarily required, it may be desired to seal such water-treated thermal inserts within a substantially liquid-impermeable material (vapor-permeable or vapor-impermeable) or package (not shown) that inhibits the exothermic coating from contacting enough oxygen to prematurely activate the exothermic reaction. To generate heat, the thermal insert is simply removed from the package, exposed to air, and inserted Into a cavity defined by the pad.

Through selective control over the supply of these reactants, a heating profile may be achieved in which an elevated temperature is reached quickly and maintained over an extended period of time. For example, an elevated temperature of from about 30° C. to about 60° C., in some embodiments from about 35° C. to about 55° C., and in some embodiments from about 37° C. to about 43° C., may be achieved in 20 minutes or less, and in some embodiments, 10 minute or less. This elevated temperature may be substantially maintained for at least about 1 hour, in some embodiments at least about 2 hours, in some embodiments at least about 4 hours, and in some embodiments, at least about 10 hours (e.g., for overnight use).

The therapeutic kit of the present invention may be used to apply uniform heat and pressure to an injured or irritated area to reduce pain, discomfort, or cramping. For example, pressure and heat may be applied to extensor muscles and tendons of the upper forearm to relieve pain and discomfort associated with epicondylitis or "tennis elbow." The application of heat and pressure across the extensor muscles and tendons prevents the firing of these muscles. In this manner, the contraction and use of these irritated or strained muscles is inhibited so as to reduce the pain and discomfort associated with tennis elbow, or other injury. The application of pressure to irritated or strained muscles may also enhance the healing process by preventing the use of these muscles and giving the muscles sufficient rest for healing to occur and avoiding further injury.

The present invention may be better understood with reference to the following examples.

EXAMPLE 1

The ability to form a thermal insert in accordance with the present invention was demonstrated. Initially, a 7"-wide roll of a 2.3 osy dual layer bonded carded web (one side contains 0.5 osy of a 100% 1.5 denier FiberVisions ESC 215 bicomponent (PE sheath/PP core) fiber with 0.55% HR6 finish and the other side contains 1.8 osy of a blend of 40% 15 denier Invista T-295 polyester fiber with 0.50% L1 finish and 60% of a 28 denier FiberVisions ESC bicomponent (PE sheath/PP core) fiber with 0.55% HR6 finish) was coated on the polyester/bicomponent fiber side. The coating formulation was prepared as follows. In a 2-gallon metal pail, 46.0 grams of METOLOSE SM-100 (Shin-Etsu Chemical Co., Ltd.) and 116.0 grams of sodium chloride (Mallinckrodt) were added to 1563.0 grams of distilled water that was stirred and heated to 70° C. The mixture was stirred and allowed to cool as the following additional ingredients were added sequentially: 186.6 grams of DUR-O-SET® Elite PE 25-220A ethylene-vinyl acetate emulsion (Celanese Emulsions), 442.2 grams of XP-5200-6 sample #05.2435503 calcium carbonate slurry (Omya), 80.0 grams of Nuchar SA-400 activated carbon (MeadWestvaco), and 1575.1 grams of A-131 iron powder (North American Hoganacs). After about 30 minutes of stirring the formulation with all ingredients, the temperature was reduced with an ice bath to about 15° C. A noticeable increase in viscosity occurred when the temperature was reduced. The calculated concentration of each component of the aqueous formulation is set forth below in Table 1.

TABLE 1

Components of the Aqueous Formulation

| Component | Calculated Amount |
|---|---|
| Iron | 39.3% |
| Activated Carbon | 2.0% |
| SM-100 | 1.2% |
| Elite PE | 2.3% |
| Calcium Carbonate | 3.8% |
| Sodium Chloride | 2.9% |
| Water | 48.5% |

The aqueous formulation was applied to the polyester/bicomponent fiber side of the dual layer bonded carded web fabric in a pilot line process using a knife coater. A 0.75 osy spunbond-meltblown-spunbond fabric was used as a carrier sheet to support the coated dual layer bonded carded web and to also keep the coating formulation from bleeding through and contacting the components of the pilot coater (e.g. rollers). The gap between the knife and steel roller that carried the fabric was set at 1100 microns. The line speed was 0.25 meters per minute. The pilot line coater contained a four-foot drier set at 145° C. that was used to partially dry the coated fabric. The partially dried coated fabric was cut into 15-inch pieces and placed in a laboratory oven at 110° C. for about 20 minutes to complete the drying step. The concentration of the components of the exothermic composition was calculated from the coated and dried fabric pieces (56.4±0.8 grams), the untreated piece of fabric (4.0 grams), and the composition of the aqueous formulation. The results are set forth below in Table 2.

TABLE 2

Components of the Exothermic Composition

| Component | Calculated Amount |
|---|---|
| Iron | 76.5% |
| Activated Carbon | 3.9% |
| SM-100 | 2.2% |
| Elite PE | 4.4% |
| Sodium Chloride | 5.6% |
| Calcium Carbonate | 7.4% |
| Solids Add-On Level | ~1310% |

A five-layered structure (1.8"×2.2") was then designed for activating the exothermic reaction. Specifically, the five-layered structure included one of the coated fabric pieces positioned on one side of a moisture holding layer, and another coated fabric piece positioned on the other side of the moisture holding layer. The uncoated side of the fabric pieces faced the moisture holding layer. The moisture holding layer was formed from 75 wt. % wood pulp fluff, 15 wt. % superabsorbent, and 10 wt. % of KoSa T255 bicomponent fiber. The moisture holding layer had a basis weight of 225 grams per square meter and a density of 0.12 grams per cubic centimeter. The wood pulp fluff was obtained from Weyerhaeuser under the name "NB416." The superabsorbent was obtained from Degussa AG under the name "SXM 9543." A "separation layer" was used to separate the moisture holding layer from the coated layer on each side. The separation layer was a fabric/film laminate with small perforated holes for allowing vapor and gas to pass while preventing passage of liquid. It was obtained from Tredegar Film Products with the label FM-425 lot no. SHBT040060.

Prior to forming the multi-layered structure, the moisture-holding layer was wetted by spraying 1.8 grams of an aqueous salt solution (10% sodium chloride in distilled water) to both sides so that the weight of the original layer was increased by a factor of 3.7. Then the separation layer was placed around it with the fabric side of the separation layer in contact with the wetted moisture-holding layer. A coated layer was then placed on each side with the uncoated side in contact with the film side of the separation layer. The total weight of the two coated layers was 5.0 grams (3.5 grams of iron). The five-layered structure was then placed inside of a pouch (2.2"×5.5") and the edges were heat sealed. The pouch was made of a nylon spunbond microporous film laminate. The laminate was obtained from Mitsubishi International Corp. and labeled TSF EDFH 5035-TYPE. The WVTR of the laminate was measured at 455 g/m$^2$/24 hrs by using the cup method (STM 2437). The pouch also contained a layer of stapleknit fabric heat sealed to the nylon spunbond side. The stapleknit fabric was produced from 20% wood pulp fluff (50% northern softwood kraft fibers/50% Alabama Pine bleached kraft softwood), 58% 1.5 denier polyester fiber (Invista Type 103), and 22% polypropylene spunbond (Kimberly-Clark Corp.). The resulting thermal insert was stored in a metallized storage bag for 48 hours prior to activating the reaction. The metallized storage bag was KAL-ML5, a two ply structure consisting of metallized polyester adhesively laminated to linear low density polyethylene, obtained from Kapak Corporation.

EXAMPLE 2

Figure 7:
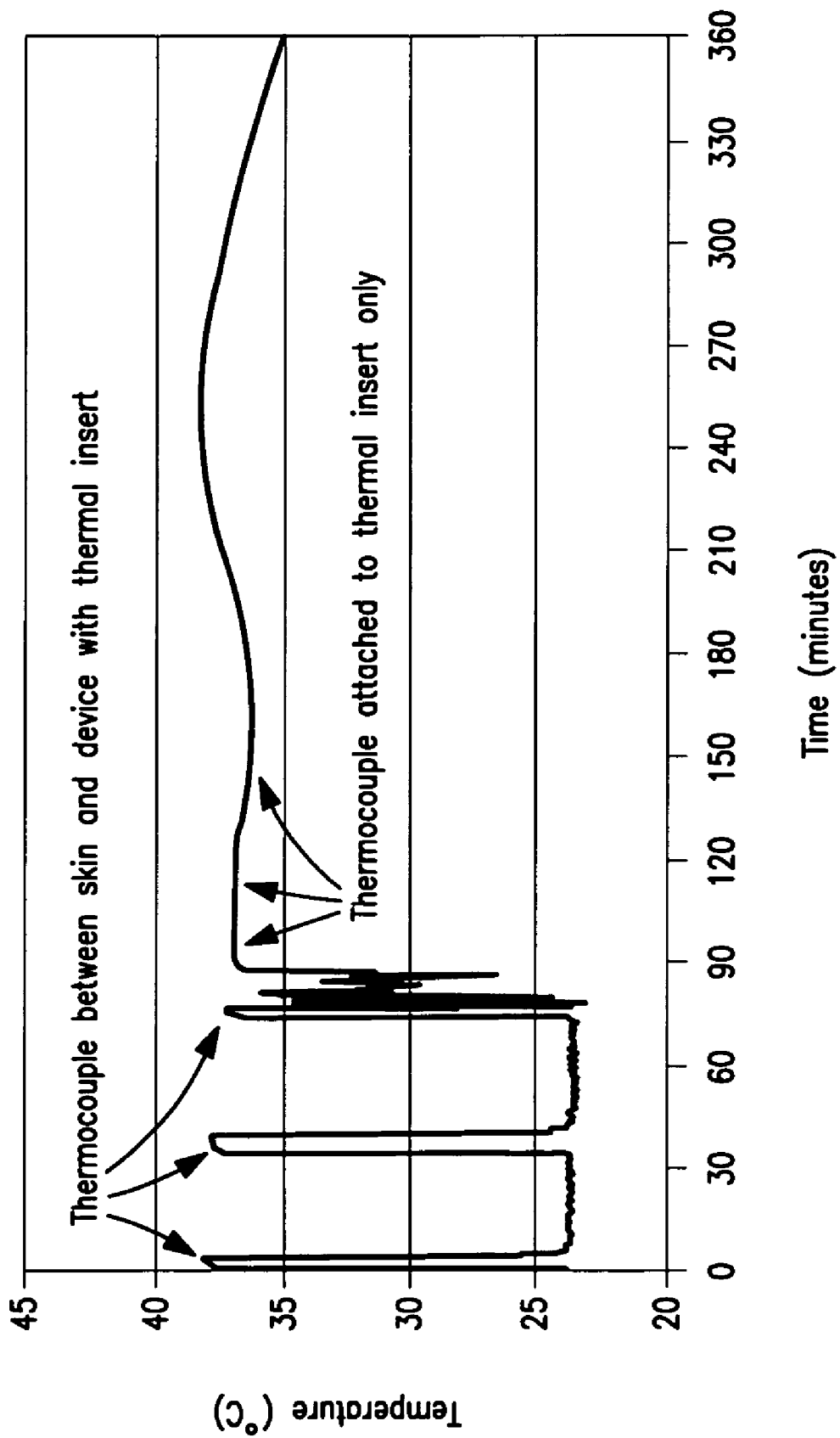
FIG. 7 illustrates the thermal response curve showing temperature (° C.) versus time (minutes) for the sample of Example 2.

The ability to assemble a therapeutic kit in accordance with one embodiment of the present invention was demonstrated. Initially, an armband having the designation Aircast® pneumatic Armband was obtained from Aircast, Inc. The Armband contained a "specialized aircell" insert attached to an extensible material. The "aircell" insert was removed and replaced with a thermal insert of Example 1. The armband containing the thermal insert was placed over a human arm so that the thermal insert was adjacent to the tendon above the elbow. A thermocouple was intermittently placed between the thermal insert and the skin. The thermocouple was wired to a data collection device to record temperature as a function of time (at 5 second intervals). After about 90 minutes, the armband was removed and the thermocouple was left in contact with the thermal insert for about 14 hours. The resulting thermal response data are shown in FIG. 7. As indicated, the temperature between the skin and the thermal insert reached about 38° C. Upon removal of the armband, the temperature of the thermal insert alone remained at 36-38° C. for an additional 4 hours. The temperature of the other human arm was measured at about 34.6° C. Therefore, the armband was successful at warming the arm from about 34 to 38° C. If necessary, the temperature provided by the thermal insert could be adjusted to provide more or less warmth, such as by changing the composition of the exothermic coating.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A therapeutic kit comprising:
   a pad that defines a cavity; and
   a thermal insert that is capable of being removably positioned within the cavity, the thermal insert comprising a substrate that contains in a single exothermic layer, an oxidizable metal, a carbon component, a binder, and an electrolytic salt, wherein the binder comprises a polymer latex having a glass transition temperature of about 30° C. or less, wherein the polymer latex is sufficiently crosslinked to be substantially insoluble in water, wherein the exothermic layer is activatable upon exposure to oxygen and moisture to generate heat.

2. The therapeutic kit of claim 1, wherein the pad contains an extensible material.

3. The therapeutic kit of claim 2, wherein the extensible material contains a film, nonwoven web, or combinations thereof.

4. The therapeutic kit of claim 2, wherein the extensible material contains an elastomeric polymer.

5. The therapeutic kit of claim 2, wherein the cavity is defined by a receptacle that is attached to the extensible material.

6. The therapeutic kit of claim 1, wherein the pad comprises one or more loops.

7. The therapeutic kit of claim 1, wherein the pad comprises one or more fasteners.

8. The therapeutic kit of claim 1, wherein the metal is iron, zinc, aluminum, magnesium, or a combination thereof.

9. The therapeutic kit of claim 1, wherein the exothermic layer is present at a solids add-on level of from about 20% to about 5000%.

10. The therapeutic kit of claim 1, wherein the exothermic layer is present at solids add-on level of from about 100% to about 1200%.

11. The therapeutic kit of claim 1, wherein the substrate contains a nonwoven web.

12. The therapeutic kit of claim 1, wherein the exothermic layer is generally free of moisture prior to activation.

13. The therapeutic kit of claim 1, wherein the thermal insert is sealed within an enclosure that inhibits the passage of oxygen to the exothermic layer prior to activation.

14. The therapeutic kit of claim 1, wherein the thermal insert further comprises an moisture-holding layer that is applied with an aqueous solution, the aqueous solution being capable of supplying moisture to the exothermic coating.

15. The therapeutic kit of claim 14, wherein the aqueous solution comprises one or more solutes.

16. The therapeutic kit of claim 15, wherein the solutes include a metal salt.

17. The therapeutic kit of claim 14, wherein the moisture-holding layer contains cellulosic fibers.

18. The therapeutic kit of claim 14, wherein the thermal device further comprises a breathable layer that is capable of regulating the amount of moisture and oxygen contacting the exothermic layer.

19. The therapeutic kit of claim 18, wherein the thermal device comprises a second substrate coated with an exothermic layer.

20. The therapeutic kit of claim 1, wherein the thermal insert further comprises a breathable layer that is capable of regulating the amount of moisture and oxygen contacting the exothermic layer.

21. The therapeutic kit of claim 1, wherein the electrolytic salt is a metal halide.

22. The therapeutic kit of claim 1, wherein the polymer latex has a glass transition temperature of from about −15° C. to about 15° C.

23. The therapeutic kit of claim 1, wherein the polymer latex includes a styrene-butadiene copolymer, polyvinyl acetate homopolymer, vinyl-acetate ethylene copolymer, vinyl-acetate acrylic copolymer, ethylene-vinyl chloride copolymer, ethylene-vinyl chloride-vinyl acetate terpolymer, acrylic polyvinyl chloride polymer, acrylic polymer, nitrile polymer, or a combination thereof.

24. A method for providing heat to a body part, the method comprising:
   providing a thermal insert comprising a substrate that contains in a single exothermic layer a carbon component, a binder, and an electrolytic salt, wherein the binder comprises a polymer latex having a glass transition temperature of about 30° C. or less, wherein the polymer latex is sufficiently crosslinked to be substantially insoluble in water, wherein the thermal insert is sealed within an enclosure that inhibits the passage of oxygen to the exothermic layer, and wherein the exothermic layer is activatable upon exposure to moisture and oxygen to generate heat, wherein the exothermic layer comprises;
   opening the enclosure and positioning the thermal insert within a cavity defined by a pad; and
   placing the pad adjacent to or near the body part.

25. The method of claim 24, wherein the exothermic layer is generally free of moisture prior to activation.

26. The method of claim 24, wherein one or more surfaces of the thermal insert reach an elevated temperature of from about 35° C. to about 55° C. in 20 minutes or less.

27. The method of claim 26, wherein the elevated temperature is maintained for at least about 1 hour.

28. The method of claim 26, wherein the elevated temperature is maintained for at least about 2 hours.

29. The method of claim 26, wherein the pad is positioned adjacent to or near an arm.

30. The therapeutic kit of claim 1, wherein the exothermic layer comprises an oxidizable metal in an amount of from about 40 wt. % to about 95 wt. % of said layer, a carbon component in an amount from about 0.01 wt. % to about 20 wt % of said layer, a binder in an amount from about 0.01 wt. % to about 20 wt. % of said layer, and an electrolytic salt in an amount from about 0.01 wt. % to about 10 wt. %.

31. The therapeutic kit of claim 1, wherein said carbon component is activated carbon.

32. The method of claim 24, wherein the polymer latex has a glass transition temperature of from about −15° C. to about 15° C.

33. The method of claim 24, wherein the polymer latex includes a styrene-butadiene copolymer, polyvinyl acetate homopolymer, vinyl-acetate ethylene copolymer, vinyl-acetate acrylic copolymer, ethylene-vinyl chloride copolymer, ethylene-vinyl chloride-vinyl acetate terpolymer, acrylic polyvinyl chloride polymer, acrylic polymer, nitrile polymer, or a combination thereof.

* * * * *